(12) United States Patent
Ashfaq (10) Patent No.: US 11,709,287 B2
(45) Date of Patent: Jul. 25, 2023

(54) WELL LOGGING TO IDENTIFY LOW RESISTIVITY PAY ZONES IN A SUBTERRANEAN FORMATION USING ELASTIC ATTRIBUTES

(71) Applicant: Saudi Arabian Oil Company, Dhahran (SA)

(72) Inventor: Muhammad Ashfaq, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 791 days.

(21) Appl. No.: 16/685,459

(22) Filed: Nov. 15, 2019

(65) Prior Publication Data

US 2021/0149068 A1  May 20, 2021

(51) Int. Cl.
| | |
|---|---|
| G01V 1/30 | (2006.01) |
| E21B 49/00 | (2006.01) |
| G01N 33/24 | (2006.01) |
| G01V 1/28 | (2006.01) |
| G01V 1/50 | (2006.01) |

(52) U.S. Cl.
CPC ............. *G01V 1/306* (2013.01); *E21B 49/00* (2013.01); *G01N 33/241* (2013.01); *G01V 1/284* (2013.01); *G01V 1/305* (2013.01); *G01V 1/50* (2013.01); *G01V 2200/16* (2013.01); *G01V 2210/1429* (2013.01); *G01V 2210/6242* (2013.01)

(58) Field of Classification Search
CPC ....... G01V 2200/16; G01V 2210/1429; G01V 2210/6242; G01V 1/50; G01V 1/305; G01V 1/284; G01V 1/306; G01N 33/241; E21B 49/00
See application file for complete search history.

(56) References Cited

U.S. PATENT DOCUMENTS

| | | | |
|---|---|---|---|
| 7,675,817 B2 | 3/2010 | Moos | |
| 8,219,319 B2 | 7/2012 | Skelt | |
| 2018/0058211 A1* | 3/2018 | Liang | ............... G01V 1/282 |

FOREIGN PATENT DOCUMENTS

| | | | | |
|---|---|---|---|---|
| CN | 107367762 | | 11/2017 | |
| EP | 0367495 | | 5/1990 | |
| GB | 2293653 A | * | 4/1996 | ............. G01N 15/08 |

OTHER PUBLICATIONS

PCT International Search Report and Written Opinion in International Appln. No. PCT/US2020/060049, dated Mar. 2, 2021, 12 pages.

Abreu et al, "Well log lithology discrimination using elastic attributes only," SEG International Exposition and 86th Annual Meeting, pp. 622-626, (2016), 5 pages.

(Continued)

*Primary Examiner* — Elias Desta
(74) *Attorney, Agent, or Firm* — Fish & Richardson P.C.

(57) ABSTRACT

Methods and systems for identifying a pay zone in a subterranean formation can include: logging a well extending into the subterranean formation including measuring bulk density, compressional wave travel time and shear wave travel time at different depths in the subterranean formation; calculating elastic attributes including acoustic impedance and compressional velocity-shear velocity ratio at different depths in the subterranean formation; and displaying and analyzing the calculated elastic attributes to identify the low resistivity pay zones.

18 Claims, 9 Drawing Sheets

(56) References Cited

OTHER PUBLICATIONS

Ayadiuno, "Investigating Low Resistivity Low Contrast Resistivity Pay in a Permo-Carboniferous Reservoir," Central Saudi Arabia, Abu Dhabi International Petroleum Exhibition and Conference, 2017, SPE-188887-MS, 17 pages.
Borland et al, "Specialized Well Log Acquisition of Formation Elastic Properties in Support of 4C Surface Seismic," International Petroleum Technology Conference, Dubai, 2007, 13 pages.
Claverie, "A New Look at Low-Resistivity and Low-Contrast (LRLC) Pay in Clastic Reservoirs," SPE Annual Technical Conference and exhibition, 2010, SPE 134402, 12 pages.
Griffiths et al., "Evaluation of Low Resistivity Pay in Carbonates—A Breakthrough," SPWLA 47th Annual Logging Symposium, Jun. 4-7, 2006, 11 pages.
Hamada, "Reservoir Fluids Identification Using Vp/Vs Ratio," Oil & Gas Science and Technology—Rev. IFP, vol. 59, No. 6, pp. 649-654, 2004, 6 pages.
Karbalaali et al, "Delineating Hydrocarbon Bearing Zones Using Elastic Impedance Inversion: A Persian Gulf Example," Iranian Journal of Oil and Gas Science and Technology, vol. 2, No. 2, pp. 8-19, 2013, 12 pages.
Krief et al, "A Petrophysical Interpretation Using the Velocities of P and S Waves," The Log Analyst, Nov.-Dec. 1990, pp. 355-369, 16 pages.
Mahaldar et al, "Unlocking Bypassed Oil in Mature PDO South Oilfields by Developing Gharif Low Resistivity Pay," Abu Dhabi International Petroleum Exhibition and Conference, 2017, SPE-188697-MS, 15 pages.
Nakken et. al "Characteristics of Drill Bit Generated Noise," SPWLA 31st Annual Logging Symposium, Jun, 24-27, 1990, abstract only, 1 page.
Poerboyo-Kelik et al, "How to Find Low Resistivity Pay in a Mature Oil Field K-Field Case Study," International Petroleum Technology Conference, 2014, IPTC 17245, 10 pages.
Potter et al, "Formation elastic parameters by deriving S-wave velocity logs," CREWES Research Report, vol. 9, pp. 10.1-10.13, 1997, 13 pages.
Williams, "The Acoustic Log Hydrocarbon Indicator," SPWLA 31st Annual Logging Symposium, Dallas, Texas, Jun. 24-27, 1990, 22 pages.
Worthington, "Recognition and Development of Low-Resistivity Pay," SPE Asia Pacific Oil and Gas Conference and Exhibition, SPE 38035, pp. 157-171, 15 pages.
GCC Examination Report issued in Gulf Cooperation Council Appln. No. 2020-40890, dated Sep. 30, 2021, 3 pages.

* cited by examiner

WELL LOGGING TO IDENTIFY LOW RESISTIVITY PAY ZONES IN A SUBTERRANEAN FORMATION USING ELASTIC ATTRIBUTES

TECHNICAL FIELD

The present disclosure generally relates to well logging, in particular well logging to identify low resistivity pay zones.

BACKGROUND

Well logging is a method of exploring a subterranean formation by making a detailed record (a well log) of the geologic formations penetrated by a borehole. The log may be based either on visual inspection of samples brought to the surface (geological logs) or on physical measurements made by instruments lowered into the hole (geophysical logs). Some types of geophysical well logs can be done during drilling, completing, producing, or abandoning a well.

A pay zone or producing zone is a layer or bed in a subterranean formation from which hydrocarbons can be produced in exploitable quantities. Pay zones can a sandstone, limestone, fractured granite or other formation that contains large hydrocarbons. It is important to identify possible pay zones during hydrocarbon exploration, for example, to support decisions on well placement.

SUMMARY

This specification describes systems and methods for identifying low resistivity pay zones in a well using elastic attributes. In general, elastic attributes are computed using elastic logs; bulk density (RHOB), compressional wave travel time (DT-P) and shear wave travel time (DT-S). The absolute and relative acoustic impedance (AI) and the velocity ratio between compressional velocity and shear velocity (Vp/Vs) are then used together to identify the low resistivity pay zones. In this context, the term absolute is used to indicate measured/computed properties and the term relative is used to indicate estimations of properties generated by fitting the measured/computed properties. For example, the absolute acoustic impedance (AI) is computed by using the measured bulk density (RHOB) and compressional wave travel time (DT-P) whereas the relative acoustic impedance (AI) is computed by fitting a regression line through absolute impedance and then using formula $AI_{rel}=AI_{abs}-AI_{reg}$.

Most pay zones can be identified by an associated change in resistivity apparent (high kicks) in well. However, some pay zones do not have an associated change in resistivity and can be overlooked by resistivity-based systems of identifying pay zones. The systems and methods described in this specification do not use the resistivity data as an input and are independent of resistivity data. This approach has been tested successfully in fifteen wells in clastic and carbonate reservoirs from different Saudi Arabian fields. The results have been validated using mud gases and the formation test data(where available)

In some aspects, methods for identifying a pay zone in a subterranean formation include: logging a well extending into the subterranean formation including measuring bulk density, compressional wave travel time and shear wave travel time at different depths in the subterranean formation; calculating elastic attributes including acoustic impedance and compressional velocity-shear velocity ratio at different depths in the subterranean formation; and displaying and analyzing the calculated elastic attributes to identify the low resistivity pay zones.

In some aspects, methods for identifying a pay zone in a subterranean formation include: deploying a logging tool in a well extending into the subterranean formation to measure bulk density, compressional wave travel time velocity and shear wave travel time velocity at different depths in the subterranean formation; calculating elastic attributes including acoustic impedance and a compressional velocity-shear velocity ratio at different depths in the subterranean formation; and displaying and analyzing the calculated elastic attributes to identify low resistivity pay zones.

Embodiments of these methods can include one or more of these methods.

In some embodiments, methods also include performing formation testing on the zones identified as possible pay zones in the subterranean formation. In some cases, methods also include producing hydrocarbons from the zones identified as possible pay zones in the subterranean formation.

In some embodiments, displaying and analyzing the calculated elastic attributes to identify the low resistivity pay zones comprises identifying zones where the compressional velocity-shear velocity ratio exceeds the acoustic impedance. In some cases, identifying zones where the compressional velocity-shear velocity ratio exceeds the acoustic impedance comprises identifying zones where an absolute compressional velocity-shear velocity ratio exceeds an absolute acoustic impedance. In some cases, identifying zones where the compressional velocity-shear velocity ratio exceeds the acoustic impedance comprises identifying zones where a relative compressional velocity-shear velocity ratio exceeds a relative acoustic impedance. In some cases, methods also include the relative acoustic impedance is computed as $AI_{rel}=AI_{abs}-AI_{reg}$ where $AI_{abs}$ is absolute acoustic impedancee, $AI_{reg}$ is acoustic impedance by fitting regression, and $AI_{rel}$ is relative acoustic impedance. In some cases, the relative compressional velocity-shear velocity ratio is computed as $VPVS_{rel}=VPVS_{abs}-VPVS_{reg}$ where $VPVS_{abs}$ is absolute VPVS velocity ratio, $VPVS_{reg}$ is the VPVS ratio from regression, and $VPVS_{rel}$ is the relative VPVS velocity ratio.

In some embodiments, logging a well extending into the subterranean formation comprises logging a pre-existing well. In some cases, at least one of the zones identified as possible pay zones in the subterranean formation is a bypassed pay zone.

In some embodiments, logging a well extending into the subterranean formation comprises using logging-while-drilling techniques.

In contrast to techniques that use mud logs and shows or formation test data (for example, drill stem test (DST) or modular formation dynamics tester (MDT) data) to identify the low resistivity pay zones, the approach described in this specification does not require any mud gases or formation testing results as prior information. This approach can also be used to identify low resistivity pay zones for wells that have already been drilled.

One of the key advantages of the proposed technique is that, resistivity by using elastic attributes which are independent of resistivity data, it can identify pay zones that are missed by resistivity-based techniques. Additionally, in contrast other methodologies, the proposed technique can be used for both clastic and carbonate reservoirs.

The details of one or more embodiments of these systems and methods are set forth in the accompanying drawings and the description to be presented. Other features, objects, and

DESCRIPTION OF DRAWINGS

Like reference symbols in the various drawings indicate like elements.

DETAILED DESCRIPTION

This specification describes systems and methods for identifying low resistivity pay zones in a well using elastic attributes. In general, elastic attributes are computed using elastic logs that measure bulk density (RHOB), compressional wave travel time (DT-P) and shear wave travel time (DT-S). The absolute and relative acoustic impedance (AI) and the velocity ratio between compressional velocity and shear velocity (Vp/Vs) are then used together to identify the low resistivity pay zones.

Most pay zones can be identified by an associated change in resistivity apparent (high kicks) in well. However, some pay zones do not have an associated change in resistivity and can be overlooked by resistivity-based systems of identifying pay zones. Low resistivity pay zones occur in both carbonate and clastic reservoirs and can cause inaccurate evaluation of pay zones that leads to the high uncertainty in water saturation (SW), net pay, and, as a result, an underestimation of oil and gas reserves. The systems and methods described in this specification do not use the resistivity data as an input and are independent of resistivity data. This approach has been tested successfully in fifteen wells in clastic and carbonate reservoirs from different Saudi Arabian fields. The results have been validated using mud gases and the formation test data (where available).

Well logs are detailed records of the geologic formations penetrated by a borehole. The oil and gas industry uses wireline logging to obtain a continuous record of a formation's rock properties with measurements of formation properties associated with the distance along the wellbore the measurements were made. Analysis of these measurements can be used to infer properties, such as hydrocarbon saturation and formation pressure, used to make drilling and production decisions.

Figure 1:
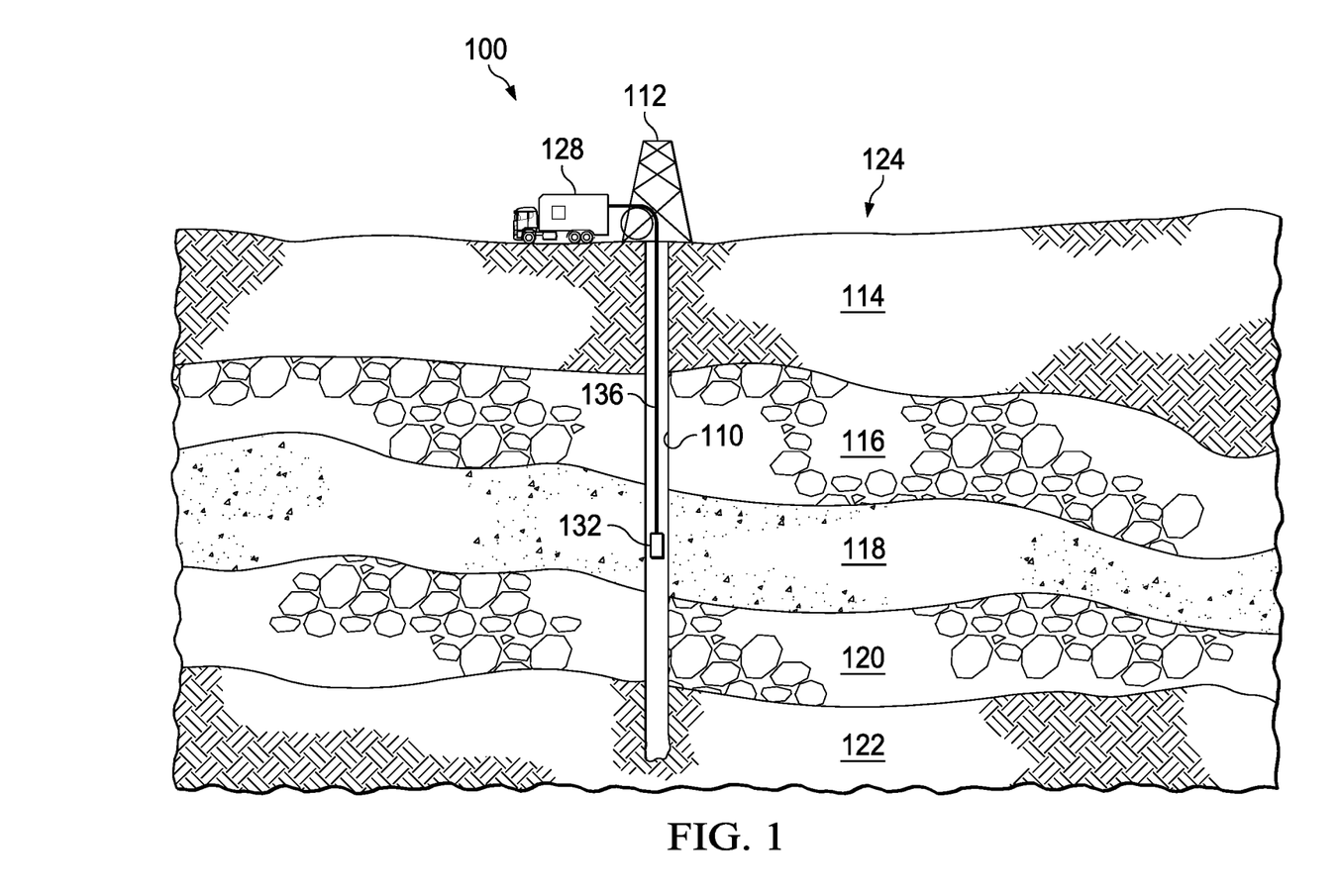
FIG. 1 is a schematic illustrating a well logging operation.

FIG. 1 illustrates a well logging operation 100 in which a wellbore 110 extends downhole from a wellhead 112. The wellbore 110 is a vertical wellbore but well logging can also be performed other wellbores, for example, slanted or horizontal wellbores. In the well logging operation 100, the wellbore 110 penetrates through five layers 114, 116, 118, 120, 122 of a subterranean formation 124. A control truck 128 lowers a logging tool 132 down the wellbore 110 on a wireline 136.

The logging tool 132 is string of one or more instruments with sensors operable to measure petrophysical properties of the subterranean formation 124. For example, logging tools can include resistivity logs, borehole image logs, porosity logs, density logs, sonic logs. Resistivity logs measure the subsurface electrical resistivity, which is the ability to impede the flow of electric current. These logs can help differentiate between formations filled with salty waters (good conductors of electricity) and those filled with hydrocarbons (poor conductors of electricity). Porosity logs measure the fraction or percentage of pore volume in a volume of rock using acoustic or nuclear technology. Acoustic logs measure characteristics of sound waves propagated through the well-bore environment. Nuclear logs utilize nuclear reactions that take place in the downhole logging instrument or in the formation. Density logs measure the bulk density of a formation by bombarding it with a radioactive source and measuring the resulting gamma ray count after the effects of Compton scattering and photoelectric absorption. Sonic logs provide a formation interval transit time, which typically a function of lithology and rock texture but particularly porosity. The logging tool consists of a piezoelectric transmitter and receiver and the time taken to for the sound wave to travel the fixed distance between the two is recorded as an interval transit time.

As the logging tool 132 travels downhole, measurements of formations properties are recorded to generate a well log. In the illustrated operation, the data is recorded at the control truck 128 in real-time. Real-time data is recorded directly against measured cable depth. In some well-logging operations, the data is recorded at the logging tool 132 and downloaded later. In this approach, the downhole data and depth data are both recorded against time The two data sets are then merged using the common time base to create an instrument response versus depth log.

In the well logging operation 100, the well logging is performed on a wellbore 110 that has already been drilled. For example, this approach might be used to identify low resistivity pay zones (for example, layer 118) that were missed by other approaches before abandoning a production well. In some operations, well logging is performed in the form of logging while drilling techniques. In these techniques, the sensors are integrated into the drill string and the measurements are made in real-time, during drilled rather using sensors lowered into a well after drilling.

Figure 2:
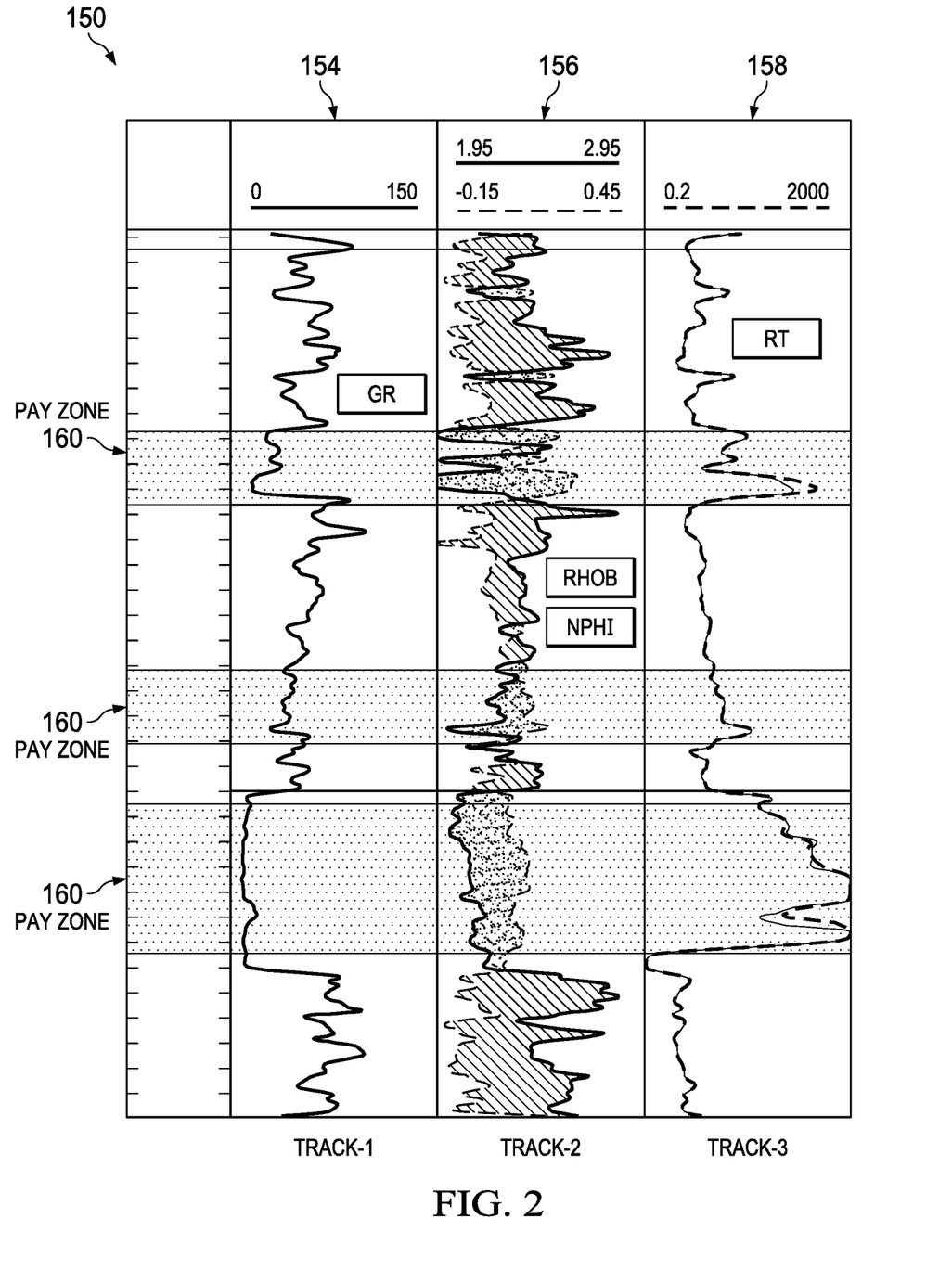
FIG. 2 is an example of a well log composite display showing a typical resistivity profile across pay zones in a conventional reservoir.

FIG. 2 is an example of a well log composite display 150 showing a typical resistivity profile across pay zones in a conventional reservoir. This well log indicates depth in feet, gamma ray (GR) in gamma-ray, American Petroleum Industry units (gapi), bulk density (RHOB) in g/cc (gram per cubic centimeter), neutron porosity (NPHI) in v/v (volume by volume), and both deep and shallow resistivity deep and shallow in ohm.m. In the well log composite display 150, the vertical axis represents depth. Track1 154 presents gamma ray data. Track2 156 presents bulk density (RHOB) and neutron porosity (NPHI). In Track2 156, the yellow shading between density and neutron porosity indicates the hydrocarbon presence. Track3 158 presents shallow and deep resistivity which tends to increase across hydrocarbon bearing pay zones 160 since hydrocarbons are less conductive than water. In this context, the difference between deep and shallow resistivity is the depth of investigation with deep resistivity reading deep in the formation away from the wellbore wall into the virgin zone or unflushed zone and shallow resistivity measuring resistivity close to the wellbore wall in the flushed zone.

This phenomenon allows use of resistivity logs to identify the hydrocarbon bearing zones in a subterranean formation. However certain characteristics, for example the presence of clay minerals, micro-porosity, conductive minerals, and fractures, can affect the resistivity logs so that the logs read too low and do not show the kick across the hydrocarbon bearing zones. In this case, the resistivity logs are misleading and potential hydrocarbon zones can easily be missed during the drilling process.

Figure 3:
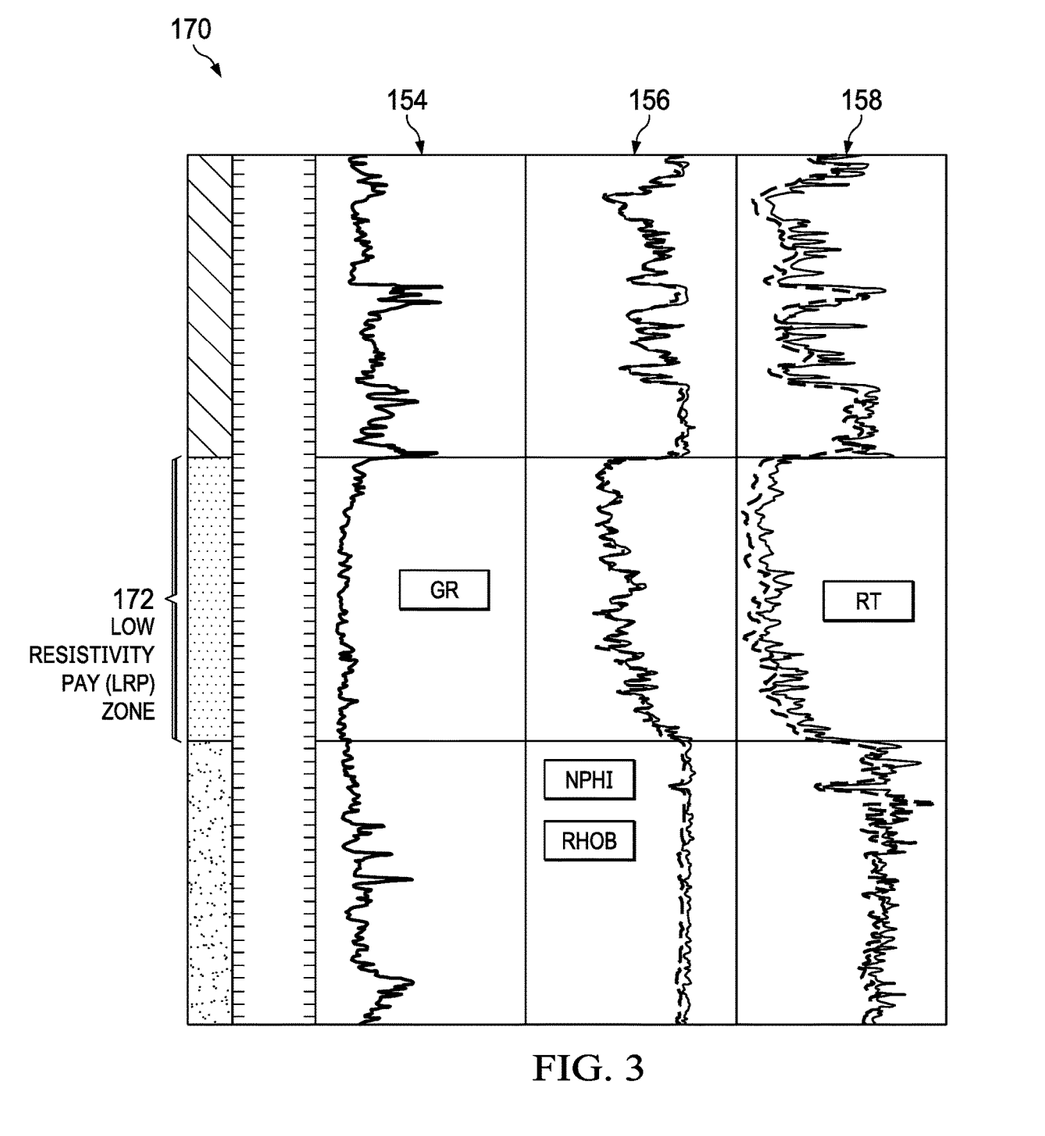
FIG. 3 is an example of a well log composite display for a formation with a low resistivity pay zone identified by mud gas analysis.

FIG. 3 is an example of a well log composite display 170 for a formation with a low resistivity pay zone identified by formation testing. In the well log composite display 170, the vertical axis represents depth. The colored bars on the left side of the well log composite display 170 present the different formation tops encountered in the wellbore with color coding that is specific to an individual formation in the wellbore. Track 1 154 presents gamma ray data. Track 2 156 presents bulk density (RHOB) and neutron porosity (NPHI). It can be noted that the density and neutron porosity closely track each other in the low resistivity pay zone. Density and neutron porosity logs that overlay each other or track each other is a typical indication of a water zone. In low resistivity pay zones caused by the water held in the micro-porosity, the density and neutron porosity logs track each other depicting a presence of water zone which is misleading and makes it very hard to identify that this is actually a pay zone. Track 3 158 presents shallow and deep resistivity. The subterranean formation represented by the well log composite display 170 includes significant micro-porosity over the hydrocarbon bearing zones that suppresses the increase of resistivity that would otherwise provide indications of the pay zone 172. The resistivity response is misleading and, as a result, the low resistivity pay zone 172 can easily be missed during drilling process if not identified using another technique.

Resolving the issues associated with low resistivity pay zones requires a workflow with four main steps. The first step is to identify the existence of the low resistivity pay zone from the first place. This is most fundamental step in the workflow. Previously, this was done using mud logs and shows from cuttings or using formation pressure and sampling data. The second step is to identify the reason of low resistivity pay zone, for example, clay minerals, micro-porosity, deep invasion, laminations, and presence of fractures. Once the exact reason of low resistivity pay is known then the next step is to implement the right solution based on reason of low resistivity pay zone. Some solutions include the integration of core data, scanning electron microscope (SEM)/x-ray diffraction (XRD) data, special core analysis (SCAL) data, petrographic data, and pore size distribution from NMR data. The forth and the last step is to validate the results. This is usually done using direct water saturation measurements from oil-based mud (OBM) cores or water saturation measurements from SCAL data.

Figure 4:
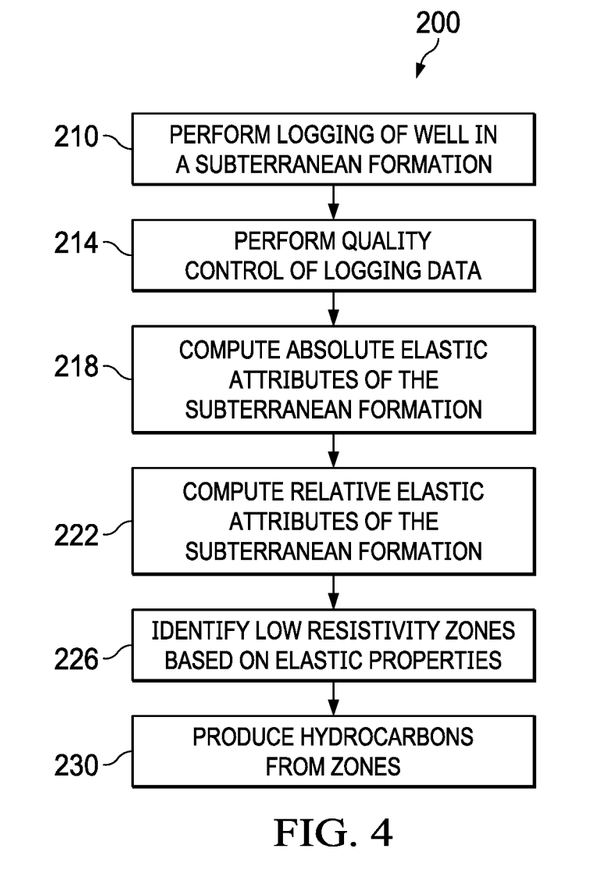
FIG. 4 is flow chart of a method for identifying low resistivity pay zones in a well using elastic attributes measured by a logging tool rather than using mud logs and shows from cuttings or using formation pressure and sampling data.

FIG. 4 is flow chart of a method 200 for identifying low resistivity pay zones in a well (step 1 of the process above) using elastic attributes calculated from logs measured by a logging tool rather than using mud logs and shows from cuttings or using formation pressure and sampling data. The first step of the method 200 is to perform well logging of a subterranean formation (step 210). For example, the well logging can be logging-while-drilling or wireline logging of an existing well. Quality control is performed to increase the likelihood that the logs reflect conditions in the subterranean formation and are consistent across the field (step 214). For example, different cross-plots can be used to identify and investigate any outliers in the data with the logs being edited, depth matched and spliced if necessary. Missing logs can be predicted using interpolation of available logs. The quality-controlled logs are then used to compute absolute elastic attributes including compressional velocity (VP), shear velocity (VS), acoustic impedance ($AI_{abs}$) and a velocity ratio ($VPVS_{abs}$) (step 218). These attributes are computed with VP=compressional velocity=1/DT-P, VS=shear velocity=1/DT-S, and $AI_{abs}$=acoustic impedance absolute=RHOB*VP. In contrast, DT-P, DT-S and RHOB are the measured logs in the wellbore.

The absolute elastic attributes are used to compute relative acoustic impedance ($AI_{rel}$) and relative velocity ratio ($VPVS_{rel}$) (step 222). The relative elastic properties can be computed by fitting a regression through absolute acoustic impedance ($AI_{abs}$) and the velocity ratio ($VPVS_{abs}$) and then calculating relative attributes using equations 1 and 2.

$$AI_{rel}=AI_{abs}-AI_{reg} \quad (1)$$

$$VPVS_{rel}=VPVS_{abs}-VPVS_{reg} \quad (2)$$

where $AI_{abs}$ is absolute acoustic impedancee, $AI_{reg}$ is acoustic impedance by fitting regression, $AI_{rel}$ is relative acoustic impedance, $VPVS_{abs}$ is absolute VPVS velocity ratio, $VPVS_{reg}$ is the VPVS ratio from regression, and $VPVS_{rel}$ is the relative VPVS velocity ratio.

Figure 5:
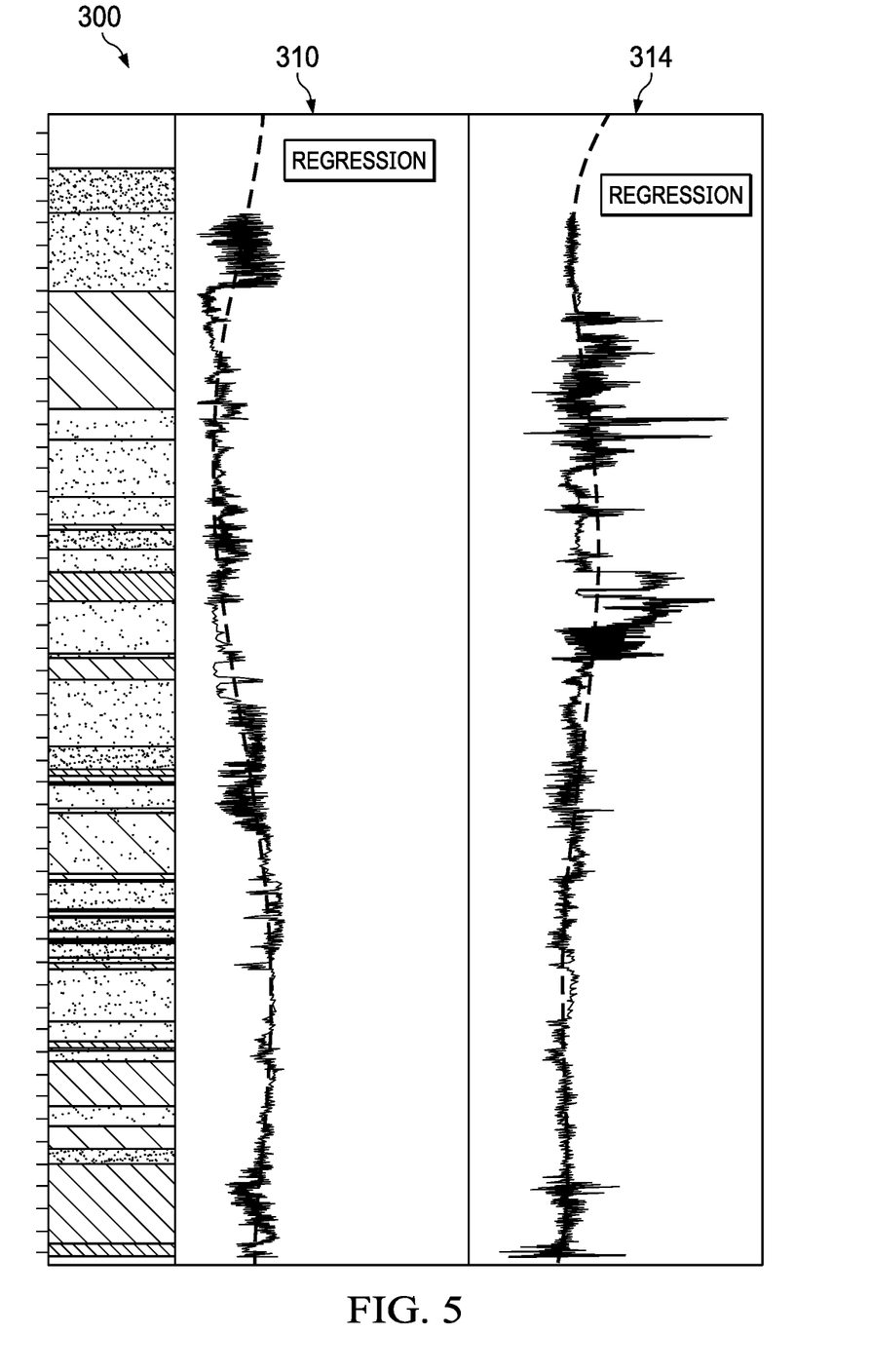
FIG. 5 is an example of a log with Track 1 displaying a regression line for acoustic impedance and Track 2 displaying a regression line for velocity ratio.

FIG. 5 is an example of a log 300 with Track 1 displaying a regression line for acoustic impedance 310 and Track 2 displaying a regression line for velocity ratio 314.

Referring again to FIG. 4, after calculation of the relative acoustic impedance and the velocity ratios, the elastic attributes are displayed and analyzed to identify the low resistivity pay zones (step 226). Depths at which the velocity ratio (VPVS) exceeds the acoustic impedance (AI) are identified as likely low resistivity pay zones. After likely pay zones have been identified, the formation testing can be planned to test these zones. The method 200 can be used to identify the low resistivity pay zones for newly drilled wells during operations and can be used to identify the bypassed pay for previously drilled wells also.

This approach can be used to identify low resistivity pay zones because the compressional and shear velocities in the formation are affected by different factors such as porosity, lithology type, compaction, and effective overburden stress. In addition to these parameters, the type of the fluid present inside the pore spaces of the rock has a significant effect on compressional velocity. Therefore, the changes in the velocity ratio VPVS and the acoustic impedance AI can be related to change in the fluid type inside the pore space of the rock.

This is true for all pay zones but only applied to low resistivity pay zones because resistivity is a more straightforward approach for normal formations. In this technique, our candidate intervals are low resistivity pay zones only even though the analysis can be applied to normal resistivity intervals with local knowledge of the reservoirs and area. This technique can be used for all formations where the low resistivity phenomenon occurs (for example, such as clastic and carbonate formations). Formations with normal resistivity behavior are straightforward and can be identified without using the proposed technique. The proposed recipe is to identify the pay zones where resistivity data is misleading and cannot be used to identify the potential hydrocarbon bearing zones.

This approach can be used to provide the basis for well drilling and testing decisions. For example, a well can be drilled and logged from the surface to the bottom of well. An asset team interprets these logs to identify the potential hydrocarbon bearing zones to be tested to check if it is feasible to produce hydrocarbons from these zone in an exploitable manner. The conventional way of identifying the hydrocarbon zones and calculating the water saturation is to use the resistivity data. Since the resistivity data is misleading in low resistivity pay zones, these zones will remain unidentified and untested. Therefore, the hydrocarbon potential for this well will be underestimated. Using this approach will identify additional pay zones for testing to determine more accurately the hydrocarbon potential of the well.

The method 200 has been tested successfully in 13 wells and 33 different reservoirs of exploration wells. The low resistivity pay zones identified by the method 200 are verified by formation test results where available. The method 200 has been successfully tested in previously drilled wells. In general, the method 200 successfully identified all the previously known and tested hydrocarbon zones as well as additional hydrocarbon zones that were overlooked using other methods.

Figure 6:
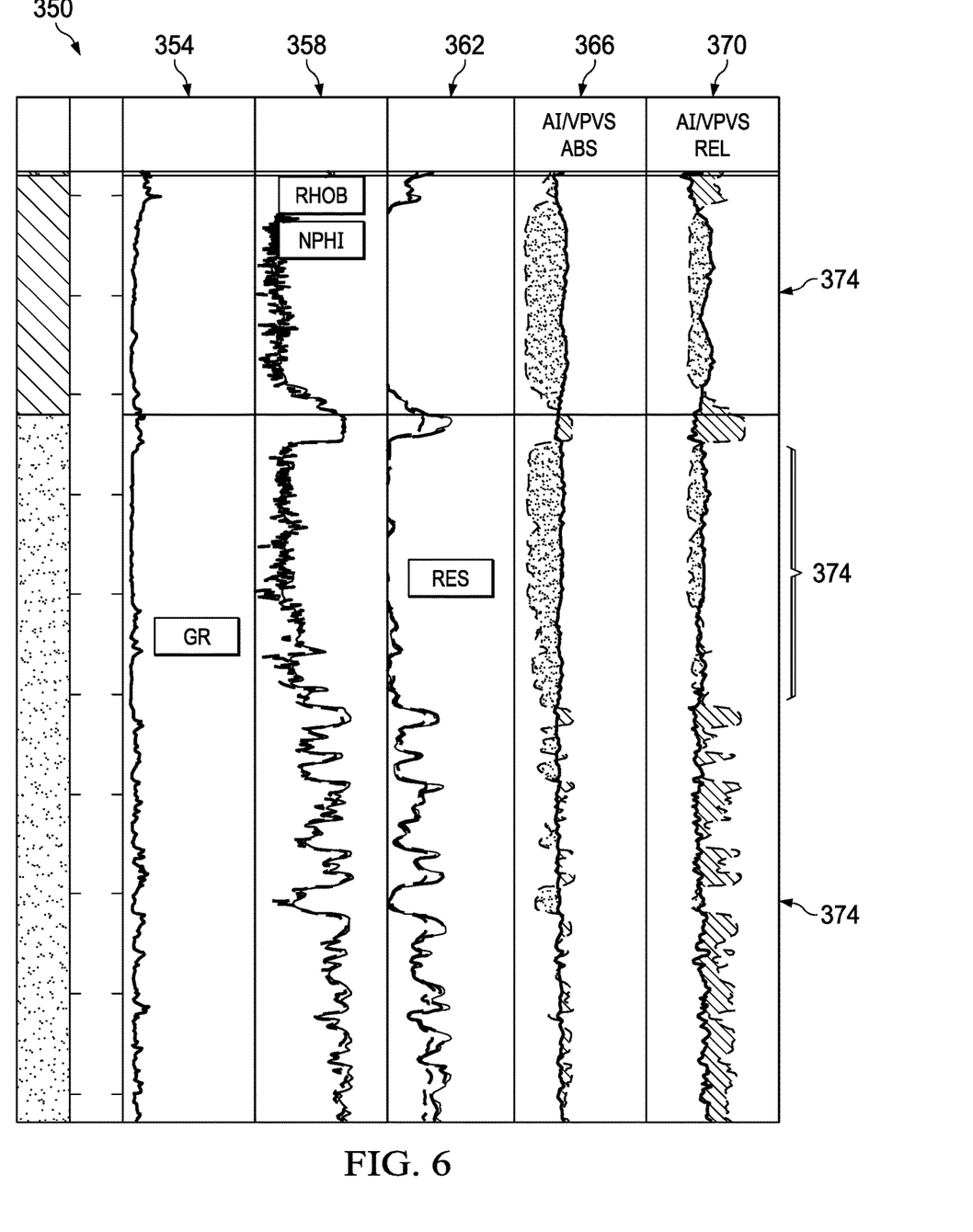
FIG. 6 is a log composite display showing the low resistivity (LRP) zones and the corresponding low resistivity kicks for one of the test formations.

FIG. 6 is a log composite display 350 showing the low resistivity (LRP) zones and the corresponding low resistivity kicks. In the log composite display 350, Track 1 displays gamma ray (GR) data 354, Track 2 displays bulk density (RHOB) and neutron porosity (NPHI) data 358, Track 3 displays shallow and deep resistivity data 362, and Track 4 displays absolute acoustic impedance (AIabs) and velocity ratio (VPVSabs) data 366, Track 5 displays relative acoustic impedance (AIrel) and the velocity ratio (VPVSrel) data 370. The yellow shading between absolute acoustic impedance (AIabs) and velocity ratio (VPVSabs) in Track 4 and relative acoustic impedance (AIrel) and the velocity ratio (VPVSrel) in Track 5 indicates pay zones 374. In Track 4 and Track 5, the black line is the acoustic impedance (AI) and the red line is the velocity ratio (VPVS). The separation between two indicates the existing of Low Resistivity Pay (LRP) zones. In some systems, shading to highlight this separation can be generated by choosing the option "shade between curves" available in the software. Depths at which both Track 4 and Track 5 show the yellow shading as an indication of low resistivity pay zones are considered as high confidence results. Sometimes the Track 4 shows more yellow shading than Track 5 or vice versa for the same low resistivity pay zone. Both tracks complement each other. Sometimes one track magnifies the separation (shallow shading) compare to other track.

Figure 7:
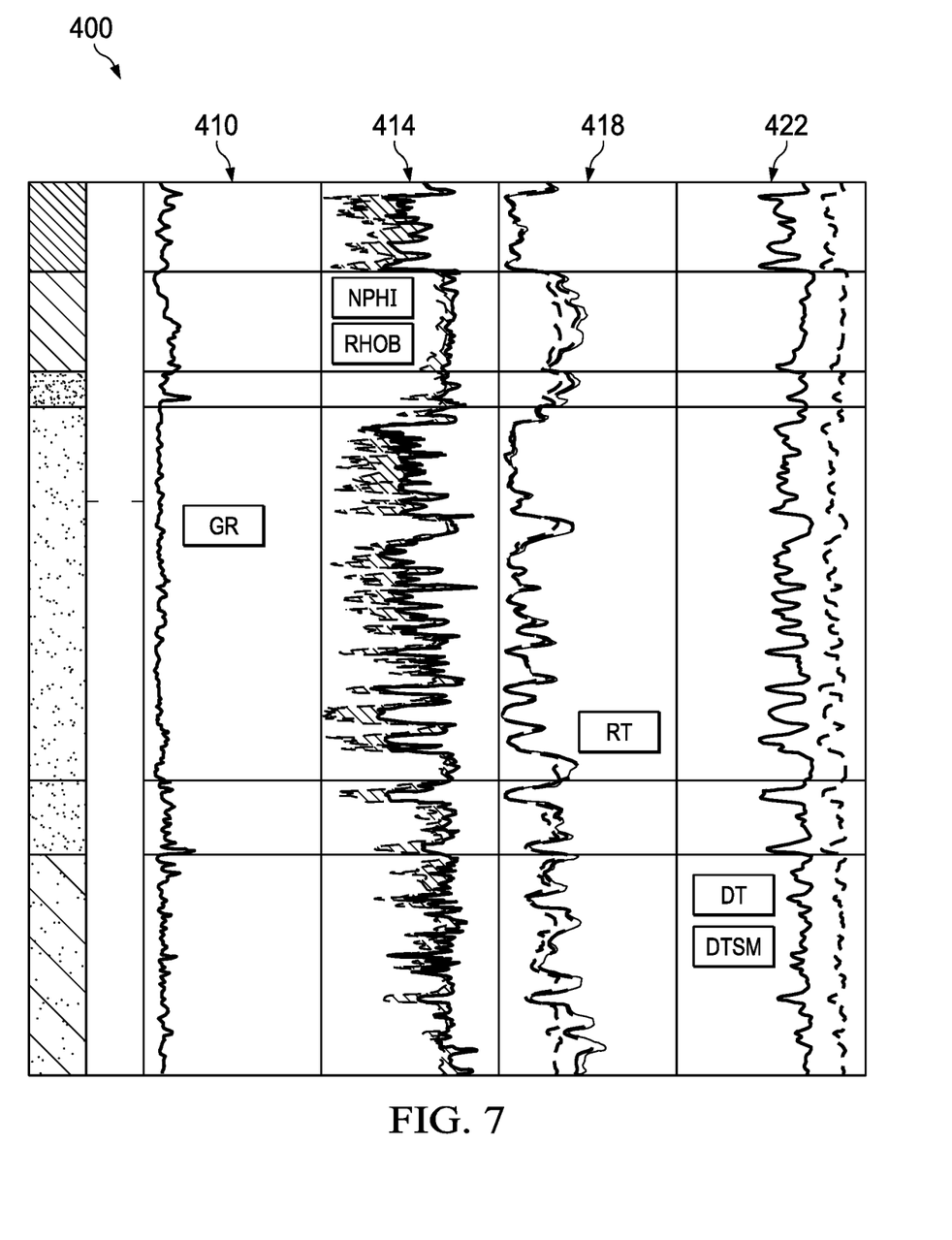
FIG. 7 is a log composite display 400 in which Track 1 displays gamma ray (GR) data 410, Track 2 displays density (RHOB) and neutron porosity (NPHI) data 414, Track 3 displays shallow and deep resistivity data 418, and Track 4 displays compressional slowness (DT-P) and shear slowness (DT-S).

FIG. 7 is a log composite display 400. This figure shows an additional track with DT-P and DT-S displayed just to show the profiles of these two measurements corresponding to low resistivity pay zones. In the log composite display 400, Track 1 displays gamma ray (GR) data 410, Track 2 displays density (RHOB) and neutron porosity (NPHI) data 414, Track 3 displays shallow and deep resistivity data 418, and Track 4 displays compressional wave travel time (DT-P) and shear wave travel time (DT-S). The resistivity logs read too low due to presence of micro-porosity over hydrocarbon bearing zones unlike the typical pay zones in conventional reservoir. The resistivity response is very misleading and as a result the pay zone can easily be missed out during the drilling process.

Figure 8:
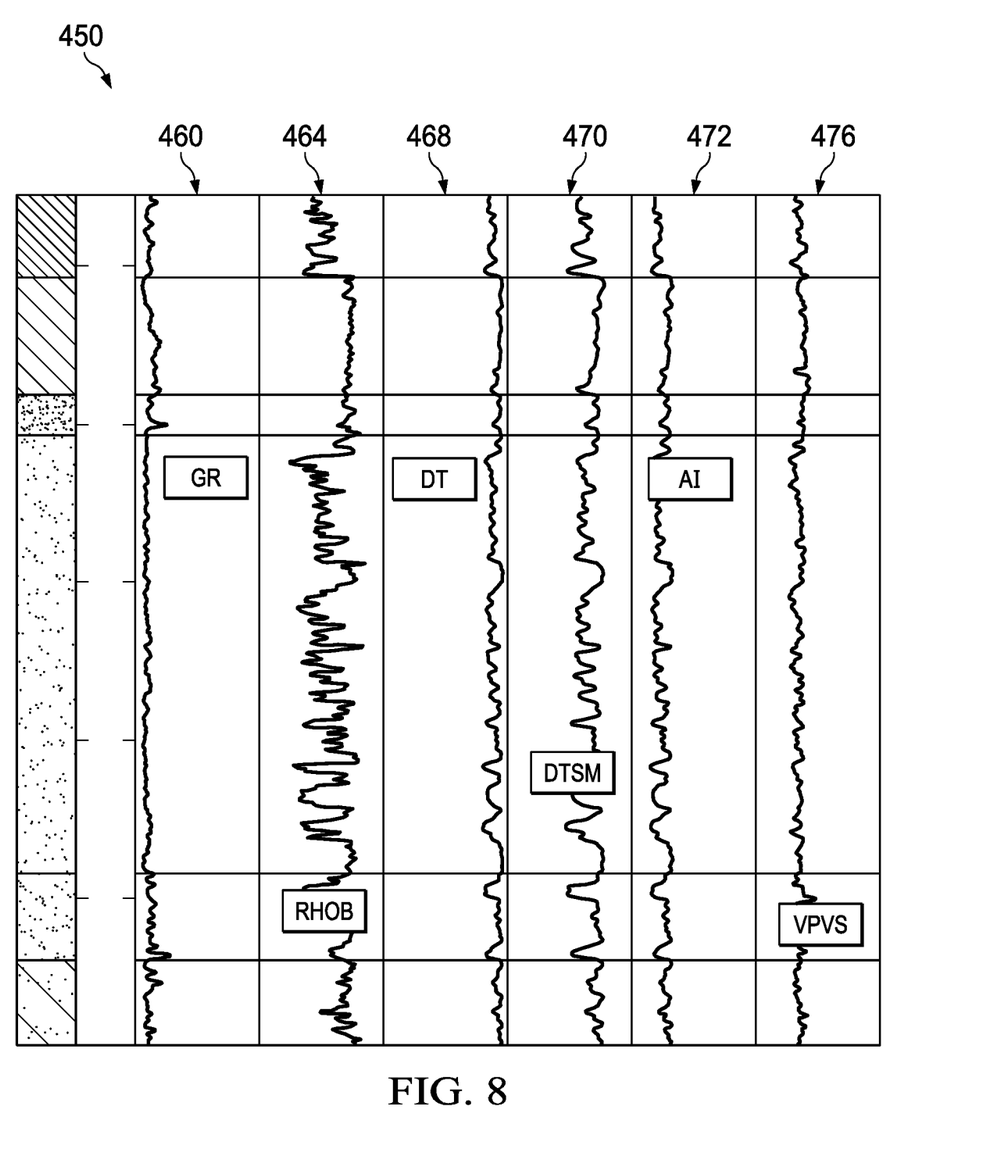
FIG. 8 is a log composite display 450.

FIG. 8 is a log composite display 450 showing the input measured curves RHOB, DT-P and DT-S & computed elastic attributes AI and VPVS from input curves. In the log composite display 450, Track 1 displays gamma ray (GR) data 460, Track 2 displays density (RHOB) data 464, Track 3 displays compressional wave travel time (DT-P) data 468, Track 4 displays shear travel time (DT-S) data 470 Track 5 displays absolute acoustic impedance (AIabs) data 472, and Track 6 displays velocity ratio (VPVSabs) data 476. The display 450 presents absolute data with each input curve in a separate track and each computed attribute AI and VPVS also in a separate track.

Figure 9:
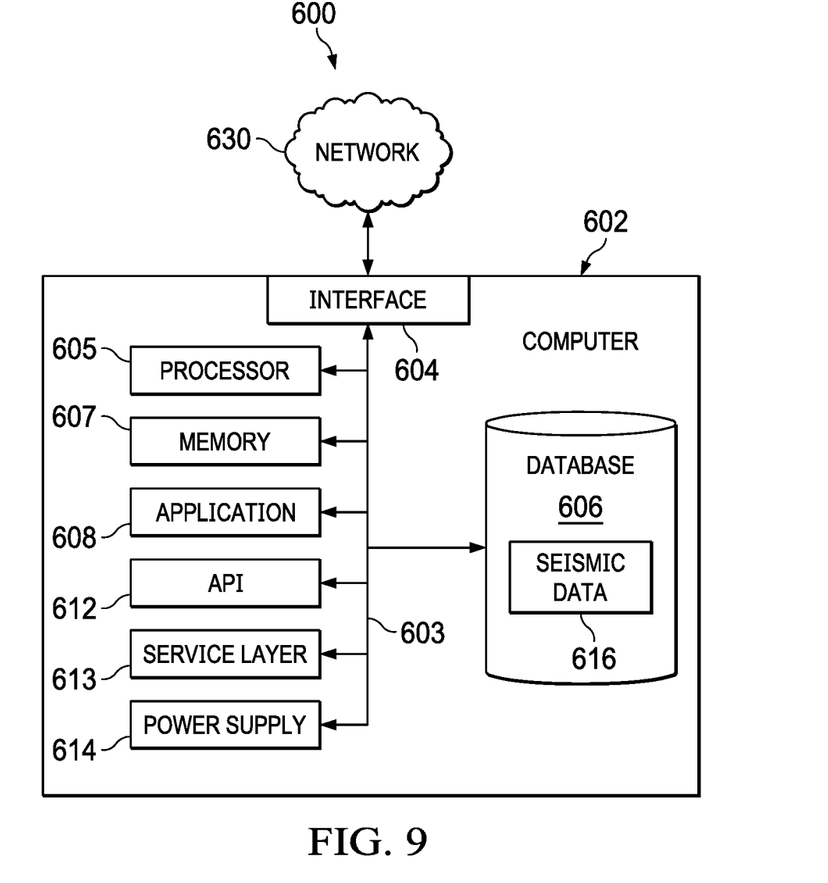
FIG. 9 is a block diagram illustrating an example computer system used to provide computational functionalities associated with described algorithms, methods, functions, processes, flows, and procedures as described in the present disclosure, according to some implementations of the present disclosure.

FIG. 9 is a block diagram of an example computer system 600 used to provide computational functionalities associated with described algorithms, methods, functions, processes, flows, and procedures described in the present disclosure, according to some implementations of the present disclosure. The illustrated computer 602 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 602 can include input devices such as keypads, keyboards, and touch screens that can accept user information. Also, the computer 602 can include output devices that can convey information associated with the operation of the computer 602. The information can include digital data, visual data, audio information, or a combination of information. The information can be presented in a graphical user interface (UI) (or GUI).

The computer 602 can serve in a role as a client, a network component, a server, a database, a persistency, or components of a computer system for performing the subject matter described in the present disclosure. The illustrated computer 602 is communicably coupled with a network 630. In some implementations, one or more components of the computer 602 can be configured to operate within different environments, including cloud-computing-based environments, local environments, global environments, and combinations of environments.

At a high level, the computer 602 is an electronic computing device operable to receive, transmit, process, store, and manage data and information associated with the described subject matter. According to some implementations, the computer 602 can also include, or be communicably coupled with, an application server, an email server, a web server, a caching server, a streaming data server, or a combination of servers.

The computer 602 can receive requests over network 630 from a client application (for example, executing on another computer 602). The computer 602 can respond to the received requests by processing the received requests using software applications. Requests can also be sent to the computer 602 from internal users (for example, from a command console), external (or third) parties, automated applications, entities, individuals, systems, and computers.

Each of the components of the computer 602 can communicate using a system bus 603. In some implementations, any or all of the components of the computer 602, including hardware or software components, can interface with each other or the interface 604 (or a combination of both), over the system bus 603. Interfaces can use an application programming interface (API) 612, a service layer 613, or a combination of the API 612 and service layer 613. The API 612 can include specifications for routines, data structures, and object classes. The API 612 can be either computer-language independent or dependent. The API 612 can refer to a complete interface, a single function, or a set of APIs.

The service layer 613 can provide software services to the computer 602 and other components (whether illustrated or not) that are communicably coupled to the computer 602. The functionality of the computer 602 can be accessible for all service consumers using this service layer. Software services, such as those provided by the service layer 613, can provide reusable, defined functionalities through a defined interface. For example, the interface can be software written in JAVA, C++, or a language providing data in extensible markup language (XML) format. While illustrated as an integrated component of the computer 602, in alternative implementations, the API 612 or the service layer 613 can be stand-alone components in relation to other components of the computer 602 and other components communicably coupled to the computer 602. Moreover, any or all parts of the API 612 or the service layer 613 can be implemented as child or sub-modules of another software module, enterprise application, or hardware module without departing from the scope of the present disclosure.

The computer 602 includes an interface 604. Although illustrated as a single interface 604 in FIG. 6, two or more interfaces 604 can be used according to particular needs, desires, or particular implementations of the computer 602 and the described functionality. The interface 604 can be used by the computer 602 for communicating with other systems that are connected to the network 630 (whether illustrated or not) in a distributed environment. Generally, the interface 604 can include, or be implemented using, logic encoded in software or hardware (or a combination of software and hardware) operable to communicate with the network 630. More specifically, the interface 604 can include software supporting one or more communication protocols associated with communications. As such, the network 630 or the hardware of the interface can be operable to communicate physical signals within and outside of the illustrated computer 602.

The computer 602 includes a processor 605. Although illustrated as a single processor 605 in FIG. 6, two or more processors 605 can be used according to particular needs, desires, or particular implementations of the computer 602 and the described functionality. Generally, the processor 605 can execute instructions and can manipulate data to perform the operations of the computer 602, including operations using algorithms, methods, functions, processes, flows, and procedures as described in the present disclosure.

The computer 602 also includes a database 606 that can hold data (for example, seismic data 616) for the computer 602 and other components connected to the network 630 (whether illustrated or not). For example, database 606 can be an in-memory, conventional, or a database storing data consistent with the present disclosure. In some implementations, database 606 can be a combination of two or more different database types (for example, hybrid in-memory and conventional databases) according to particular needs, desires, or particular implementations of the computer 602 and the described functionality. Although illustrated as a single database 606 in FIG. 6, two or more databases (of the same, different, or combination of types) can be used according to particular needs, desires, or particular implementations of the computer 602 and the described functionality. While database 606 is illustrated as an internal component of the computer 602, in alternative implementations, database 606 can be external to the computer 602.

The computer 602 also includes a memory 607 that can hold data for the computer 602 or a combination of components connected to the network 630 (whether illustrated or not). Memory 607 can store any data consistent with the present disclosure. In some implementations, memory 607 can be a combination of two or more different types of memory (for example, a combination of semiconductor and magnetic storage) according to particular needs, desires, or particular implementations of the computer 602 and the described functionality. Although illustrated as a single memory 607 in FIG. 6, two or more memories 607 (of the same, different, or combination of types) can be used according to particular needs, desires, or particular implementations of the computer 602 and the described functionality. While memory 607 is illustrated as an internal component of the computer 602, in alternative implementations, memory 607 can be external to the computer 602.

The application 608 can be an algorithmic software engine providing functionality according to particular needs, desires, or particular implementations of the computer 602 and the described functionality. For example, application 608 can serve as one or more components, modules, or applications. Further, although illustrated as a single application 608, the application 608 can be implemented as multiple applications 608 on the computer 602. In addition, although illustrated as internal to the computer 602, in alternative implementations, the application 608 can be external to the computer 602.

The computer 602 can also include a power supply 614. The power supply 614 can include a rechargeable or non-rechargeable battery that can be configured to be either user- or non-user-replaceable. In some implementations, the power supply 614 can include power-conversion and management circuits, including recharging, standby, and power management functionalities. In some implementations, the power-supply 614 can include a power plug to allow the computer 602 to be plugged into a wall socket or a power source to, for example, power the computer 602 or recharge a rechargeable battery.

There can be any number of computers 602 associated with, or external to, a computer system containing computer 602, with each computer 602 communicating over network 630. Further, the terms "client," "user," and other appropriate terminology can be used interchangeably, as appropriate, without departing from the scope of the present disclosure. Moreover, the present disclosure contemplates that many users can use one computer 602 and one user can use multiple computers 602.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non transitory, computer-readable computer-storage medium for execution by, or to control the operation of, data processing apparatus. Alternatively, or additionally, the program instructions can be encoded in/on an artificially generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example, LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure. Accordingly, other embodiments are within the scope of the following claims.

What is claimed is:

1. A method for identifying a pay zone in a subterranean formation, the method comprising:
   logging, by a computing device of a control system in communication with a logging tool, a well extending into the subterranean formation including measuring bulk density, compressional wave travel time and shear wave travel time at different depths in the subterranean formation;
   calculating, by the computing device, elastic attributes including acoustic impedance and compressional velocity-shear velocity ratio at different depths in the subterranean formation;
   displaying and analyzing, by the computing device, the calculated elastic attributes to identify the low resistivity pay zones where the compressional velocity-shear velocity ratio exceeds the acoustic impedance; and
   controlling, by the computing device, performance of formation testing on the zones identified as possible pay zones in the subterranean formation.

2. The method of claim 1, further comprising producing hydrocarbons from the zones identified as possible pay zones in the subterranean formation.

3. The method of claim 1, wherein identifying zones where the compressional velocity-shear velocity ratio exceeds the acoustic impedance comprises identifying zones where an absolute compressional velocity-shear velocity ratio exceeds an absolute acoustic impedance.

4. The method of claim 3, wherein the relative acoustic impedance is computed as $$AI_{rel}=AI_{abs}-AI_{reg}$$

where $MI_{abs}$ is absolute acoustic impedancee, $AI_{reg}$ is acoustic impedance by fitting regression, and $AI_{rel}$ is relative acoustic impedance.

5. The method of claim 1, wherein identifying zones where the compressional velocity-shear velocity ratio exceeds the acoustic impedance comprises identifying zones where a relative compressional velocity-shear velocity ratio exceeds a relative acoustic impedance.

6. The method of claim 5, wherein the relative compressional velocity-shear velocity ratio is computed as $$VPVS_{rel}=VPVS_{abs}-VPVS_{reg} \qquad (2)$$

where $VPVS_{abs}$ is absolute VPVS velocity ratio, $VPVS_{reg}$ is the VPVS ratio from regression, and $VPVS_{rel}$ is the relative VPVS velocity ratio.

7. The method of claim 1, wherein logging a well extending into the subterranean formation comprises logging a pre-existing well.

8. The method of claim 6, wherein at least one of the zones identified as possible pay zones in the subterranean formation is a bypassed pay zone.

9. The method of claim 1, wherein logging a well extending into the subterranean formation comprises using logging-while-drilling techniques.

10. A method for identifying a pay zone in a subterranean formation, the method comprising:
    deploying a logging tool in a well, the logging tool being controlled by a computing device of a control system and extending into the subterranean formation to measure i) bulk density, ii) compressional wave travel time velocity, and iii) shear wave travel time velocity at different depths in the subterranean formation;
    calculating, by the computing device, elastic attributes including acoustic impedance and a compressional velocity-shear velocity ratio at different depths in the subterranean formation;
    displaying and analyzing, by the computing device, the calculated elastic attributes to identify low resistivity pay zones where the compressional velocity-shear velocity ratio exceeds the acoustic impedance; and
    controlling, by the computing device, performance of formation testing on the zones identified as possible pay zones in the subterranean formation.

11. The method of claim 10, further comprising producing hydrocarbons from the zones identified as possible pay zones in the subterranean formation.

12. The method of claim 10, wherein identifying zones where the compressional velocity-shear velocity ratio exceeds the acoustic impedance comprises identifying zones where an absolute compressional velocity-shear velocity ratio exceeds an absolute acoustic impedance.

13. The method of claim 10, wherein identifying zones where the compressional velocity-shear velocity ratio exceeds the acoustic impedance comprises identifying zones where a relative compressional velocity-shear velocity ratio exceeds a relative acoustic impedance.

14. The method of claim 13, wherein the relative acoustic impedance is computed as $$AI_{rel}=AI_{abs}-AI_{reg}$$

where $AI_{abs}$ is absolute acoustic impedancee, $AI_{reg}$ is acoustic impedance by fitting regression, and $AI_{rel}$ is relative acoustic impedance.

15. The method of claim 14, wherein the relative compressional velocity-shear velocity ratio is computed as $$VPVS_{rel}=VPVS_{abs}-VPVS_{reg}$$

where $VPVS_{abs}$ is absolute VPVS velocity ratio, $VPVS_{reg}$ is the VPVS ratio from regression, and $VPVS_{rel}$ is the relative VPVS velocity ratio.

16. The method of claim 10, wherein logging a well extending into the subterranean formation comprises logging a pre-existing well.

17. The method of claim 10, wherein logging a well extending into the subterranean formation comprises using logging-while-drilling techniques.

18. The method of claim 10, further comprising displaying the acoustic impedance and the compressional velocity-shear velocity ratio on a single track of a well log.

* * * * *

UNITED STATES PATENT AND TRADEMARK OFFICE
CERTIFICATE OF CORRECTION

PATENT NO. : 11,709,287 B2
APPLICATION NO. : 16/685459
DATED : July 25, 2023
INVENTOR(S) : Muhammad Ashfaq It is certified that error appears in the above-identified patent and that said Letters Patent is hereby corrected as shown below:

In the Claims

In Column 15, Line 13, Claim 4, please replace "$MI_{abs}$" with -- $AI_{abs}$ --.

In Column 15, Line 13, Claim 4, please replace "impedancee," with -- impedance, --.

In Column 16, Line 27, Claim 14, please replace "impedancee," with -- impedance, --.

In Column 16, Line 27, Claim 14, please replace "$A1_{reg}$" with -- $AI_{reg}$ --.

In Column 16, Line 28, Claim 14, please replace "$A1_{rel}$" with -- $AI_{rel}$ --.

In Column 16, Line 33, Claim 15, please replace with
-- $VPVS_{rel} = VPVS_{abs} - VPVS_{reg}$       (2) --.

Signed and Sealed this
Thirteenth Day of May, 2025

Coke Morgan Stewart
*Acting Director of the United States Patent and Trademark Office*